United States Patent [19]
Shih

[11] Patent Number: 6,158,790
[45] Date of Patent: Dec. 12, 2000

[54] CLIPPING DEVICE FOR A SYRINGE CAP OR THE LIKE

[76] Inventor: Wun-Chang Shih, No. 4, Alley 5, Lane 16, San-Min Road, Chiung-Lin, Hsinchu, Taiwan

[21] Appl. No.: 09/290,138

[22] Filed: Apr. 13, 1999

[51] Int. Cl.⁷ .................. A61M 5/32; B67B 7/00
[52] U.S. Cl. .................. 294/34; 81/3.42; 128/919; 294/103.1
[58] Field of Search .............. 294/11, 16, 27.1, 294/31.2, 34, 99.1, 99.2, 100, 103.1; 81/3.4, 3.42, 3.8, 13, 44, 487; 128/919; 604/192

[56] References Cited

U.S. PATENT DOCUMENTS

| | | | |
|---|---|---|---|
| 2,382,145 | 8/1945 | Hadley | 294/103.1 |
| 2,448,815 | 9/1948 | Mattocks | 81/3.42 |
| 2,486,523 | 11/1949 | Deschenes | 81/3.42 |
| 2,716,910 | 9/1955 | Guerinet | 294/103.1 X |
| 2,748,640 | 6/1956 | Alexander | 81/3.42 |
| 3,628,405 | 12/1971 | Fleisher | 81/3.42 |
| 4,938,514 | 7/1990 | D'Addezio | 294/16 |
| 4,950,015 | 8/1990 | Nejib et al. | 294/31.2 X |
| 5,143,414 | 9/1992 | Rosellini | 294/99.2 |

*Primary Examiner*—Johnny D. Cherry
*Attorney, Agent, or Firm*—Ladas & Parry

[57] ABSTRACT

A clipping device for a cap needle or the like is disclosed. The device comprises a main body and a pushing block, wherein a cylindrical insertion hole is formed at one end of the main body and a rectangular slot is formed adjacent to and overlapping with the edge of the insertion hole. The pushing block is slidably mounted within the slot, which comprises a lower section and an upper section and is formed integrally as a block body. One end of the lower section is a clipping section, which is used to clip and hold the syringe cap. The pushing block is pushed away with a finger, and a syringe cap can be clipped and held by means of the clipping section when the syringe cap is within the insertion hole.

7 Claims, 3 Drawing Sheets

CLIPPING DEVICE FOR A SYRINGE CAP OR THE LIKE

BACKGROUND OF THE INVENTION (a) Field of the Invention

The present invention relates to a clipping device, particularly, to a clipping device for holding a syringe cap or the like so that the user can easily enclose a syringe needle with the device. Thus, accidental injuries caused by the tip of the needle are avoided.

(b) Description of the Prior Art

Before the doctors or the nurses use a syringe to perform an injection on a patient, they need to first remove a syringe cap from the syringe, and then inject a liquid medication via a syringe needle into the patient. After the injection, the syringe cap is capped onto the needle for disposal. Heretofore, no clipping device used to clip and hold the syringe cap has been disclosed. Thus, the doctors or the nurses have to hold the syringe cap with one hand and hold the syringe with the other in order to remove the cap from or to mount the cap onto the syringe. However, due to the small opening of the syringe cap, the doctors or the nurses can easily be injured by the needle as a result of their carelessness or being accidentally knocked by someone while handling the syringe. In cases where the syringe was used on a patient with infectious diseases such as AIDS, then the disease may be transmitted to the doctors or the nurses.

SUMMARY OF THE INVENTION

It is an objective of the present invention to provide a clipping device for a syringe cap or the like, which solves the above drawbacks. The present clipping device is used to clip and hold the syringe cap when the cap is to be removed from or enclosed onto the syringe. The user of the present device does not need to directly contact the syringe cap. Thus, accidental injuries by the tip of the syringe needle are avoided and infection by a fatal disease as a result of a contaminated syringe needle shall not occur.

In accordance with the present invention, a clipping device for a syringe cap or the like is disclosed. The device comprises a main body and a pushing block, wherein an insertion hole to allow the insertion of the syringe cap is formed at one end of the main body. A slot of a substantially rectangular shape is formed along the surface of the main body, adjacent to and partially overlapping the insertion hole. A pair of protruded edges are formed on the longitudinal edges of the slot. The pushing block is slidably mounted within the slot and comprises a lower section and an upper section. The upper section is a block body, and the lower section is a rectangular plate having a clipping section being formed at one end thereof and adjacent to the edge of the insertion hole. The pushing block is pushed away with fingers, and the syringe cap can be clipped by means of the clipping section when the syringe cap is within the insertion hole of the clipping device.

DETAILED DESCRIPTION OF THE PREFERRED EMBODIMENT

Figure 1:
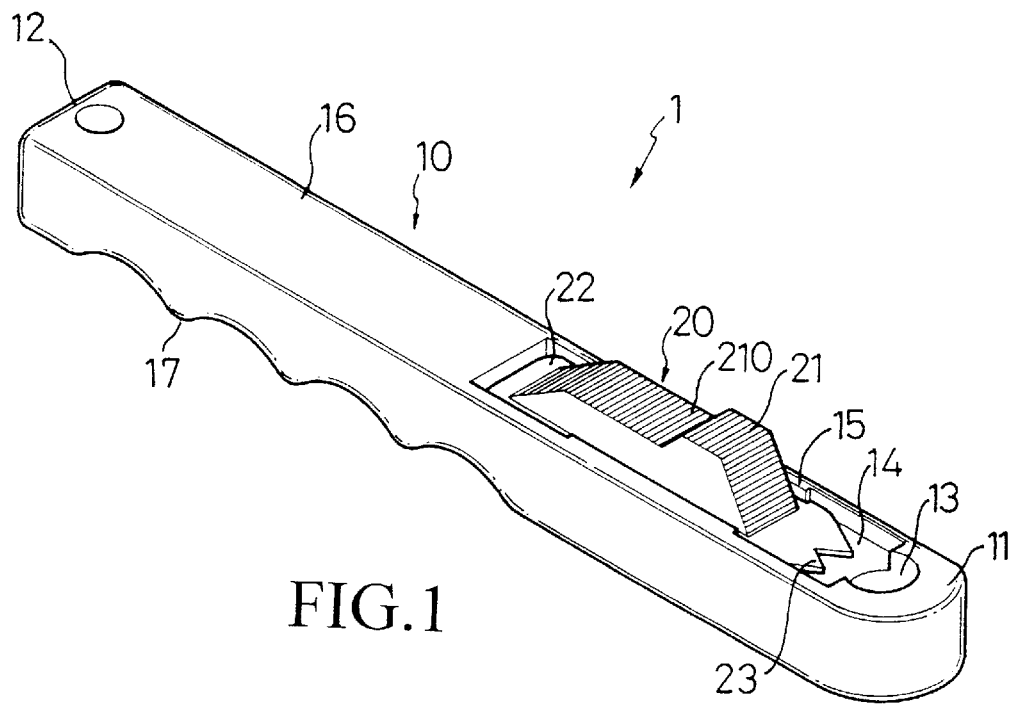
FIG. 1 is a perspective view of a clipping device for a syringe cap in accordance with the present invention.
Figure 2:
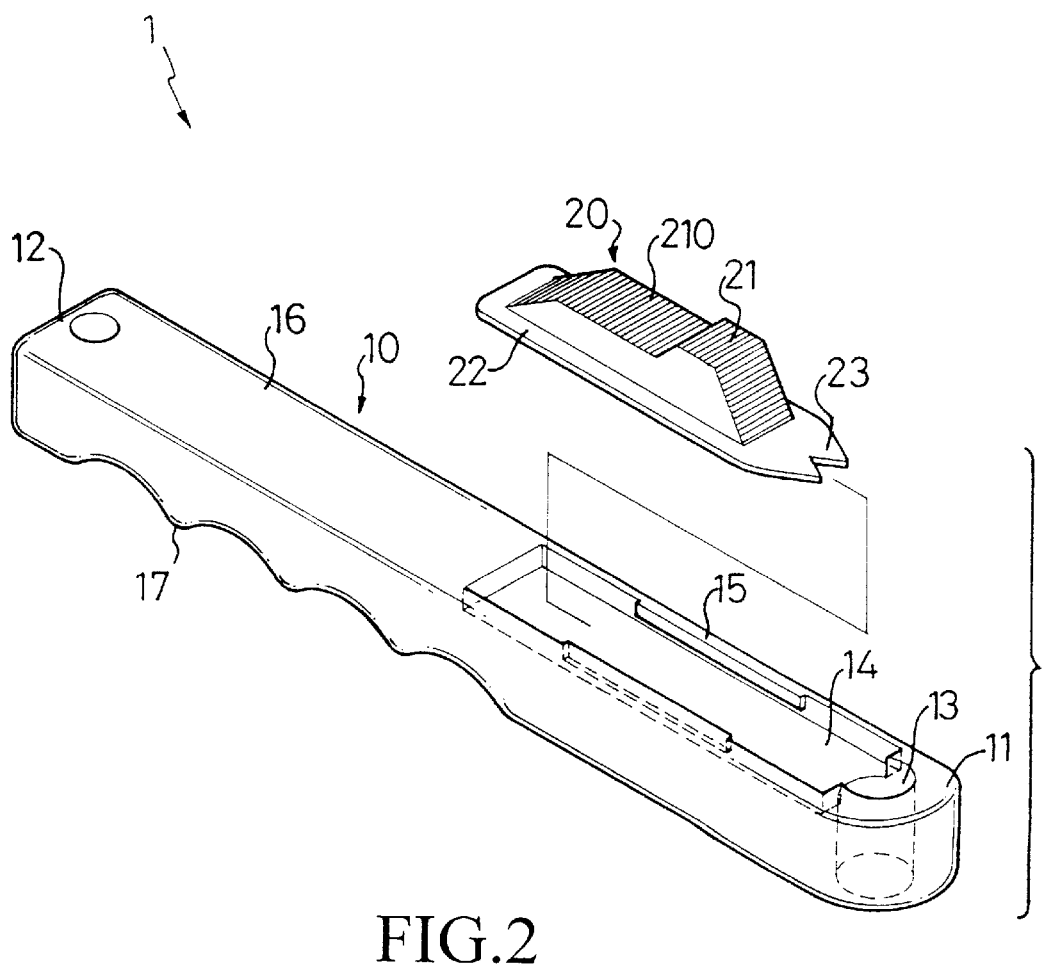
FIG. 2 is an exploded view of the clipping device for a syringe cap showing the pushing block in accordance with the present invention.

Referring to FIGS. 1 and 2, a clipping device 1 for clipping a syringe cap or the like is shown. In accordance with the present invention, the clipping device 1 is of a substantially rectangular shape comprising a main body 10 and a pushing block 20. The main body 10 further comprises a front end 11, a rear end 12, a top surface and a bottom surface. The front end 11, or the first end 11, of the main body 10 is arc-shaped and a cylindrical insertion hole 13 is provided at the front end 11 of the main body 10. The top surface of the main body 10, adjacent to the insertion hole 13 and partially overlapping the edge of the insertion hole 13, is provided with a rectangular slot 14 having the same axis as that of the main body 10. Along an upper edge of both longitudinal sides of the slot 14, a protruded edge 15 is respectively provided. The rear end 12, or the second end 12, of the main body 10 is a handle section 16 and the corresponding bottom surface of the main body 10 has a plurality of wave-like structures 17 which facilitate the holding of the clipping device 1 by the user.

In accordance with the present invention, the pushing block 20 comprises an upper section 21 and a lower section 22. The upper section 21 is a step-like block facilitating the pushing with the fingers and has a top surface and a bottom surface. On the top surface of the upper section 21, a plurality of engraved elements 210 for increasing the frictional force for the fingers in pushing are provided. The lower section 22 of the pushing block 20 is a flat rectangular plate, which is slightly smaller in size as compared with that of the slot 14, but slightly larger in size as compared with that of the upper section 21. Thus, an edge of the lower section 22 protrudes beyond the bottom surface of the upper section 21. In addition, a saw-like clipping section 23 is formed at a front end of the lower section 22.

Figure 3:
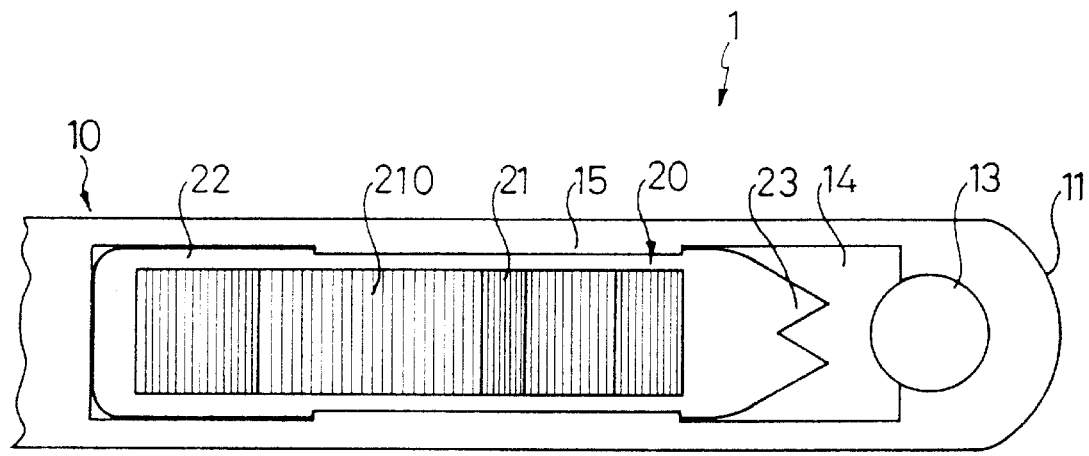
FIG. 3 is a top view of the clipping device for a syringe cap in accordance with the present invention.

As shown in FIGS. 1 and 3, the pushing block 20 is mounted within the slot 14 of the main body 10. As the width and length of the lower section 22 are smaller than those of the slot 14, the edge of the lower section 22 is sufficiently extended and insertable below the protruded edges 15 such that a guiding mechanism is formed. The lower section 22 is slidably moved and is confined by the protruded edges 15 within the slot 14 such that the lower section 22 does not dislocate from the slot 14.

Figure 4:
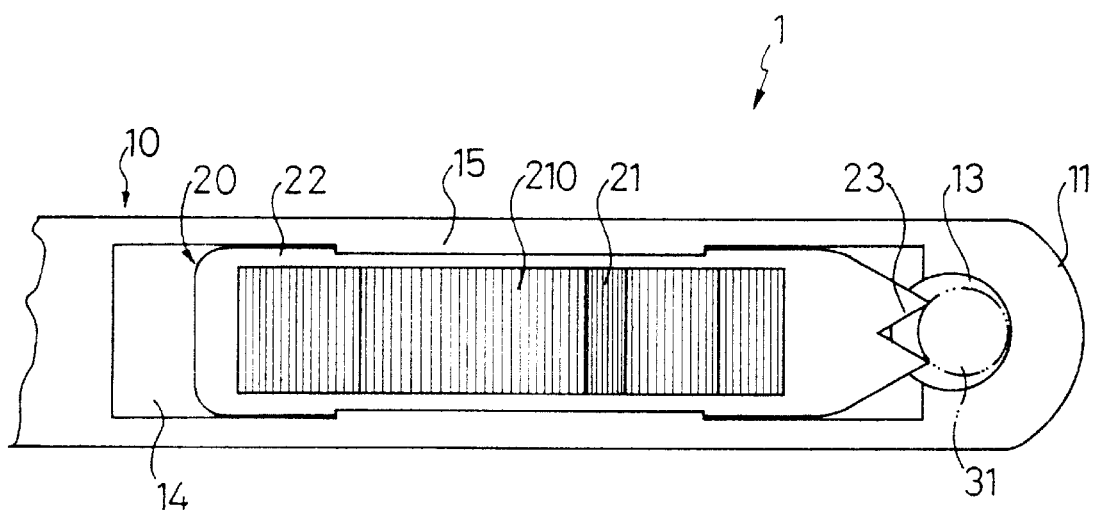
FIG. 4 is a top view showing the clipping of a syringe cap by the clipping device in accordance with the present invention.
Figure 5:
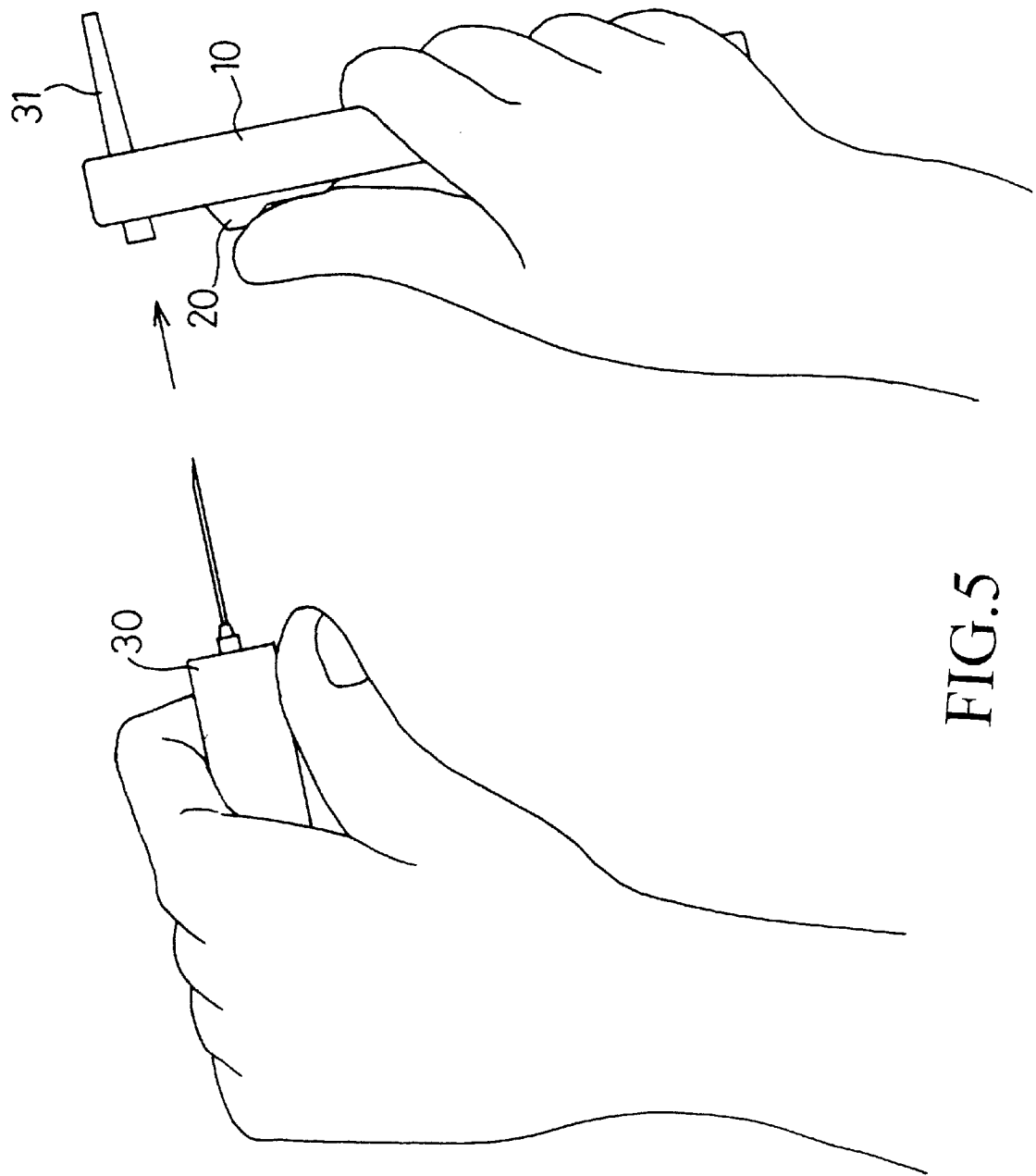
FIG. 5 is a schematic view showing the use of the clipping device with the syringe cap being clipped by the device.

FIG. 4 and FIG. 5 show the use of the clipping device 1 in accordance with the present invention. Firstly, one hand of the user holds the device 1 at the handle 16. The front end of the syringe cap 31 is inserted into the insertion hole 13, and one finger, for instance, the thumb of the used, is used to push the pushing block 20 towards the front end 11 of the main body 10. When the clipping section 23 urges the syringe cap 31, the pushing block 20 is firmly clipped onto the cap 31. The cap 31 is then dislocated from the syringe 30 by separating the device 1 from the syringe 30.

After the syringe 30 has been used to perform an injection on a patient, the user uses the clipping device 1 to first clip onto the cap 31. That is, the user exerts a force at the pushing block 20, and then inserts the front end of the syringe 30 (with a needle) into the cap 31. When the front end of the syringe 30 has been enclosed with the cap 31, the pushing block 20 is pushed backward. Thus, the combined syringe 30 with the syringe cap 31 is then released from the clipping device 1 for safety disposal.

In accordance with the present invention, there is a distance between the insertion hole 13 and the pushing block 20. Therefore, the risk of injury by the syringe needle in the process of enclosing the cap 31 onto the syringe needle of the syringe 30 or removing the cap 31 from the syringe needle is thus avoided.

Although the invention has been described with reference to the preferred embodiment, it will be obvious to those skilled in the art that various changes and modifications may be made without departing from the scope of the invention as recited in the claims. For example, the clipping section 23 can be made into other shapes as long as it can clip the syringe cap 31, and the pushing block 20 as well as the handle 16 may be made into other forms of configuration.

What is claimed is:

1. A clipping device for a syringe cap or the like comprising:

(a) a main body of a substantially rectangular shape, having a first end, a second end, a top surface and a bottom surface, a cylindrical insertion hole being formed at said first end, a substantially rectangular slot being formed on said top surface and adjacent to said insertion hole, said slot having two longitudinal edges and having the same axis as said main body, and a guiding mechanism being provided on said slot; and (b) a pushing block having a clipping section at one end adjacent to said insertion hole, said pushing block being confined by said guiding mechanism and being slidably movable within said slot.

2. The clipping device as set forth in claim 1, wherein said bottom surface of said second end of said main body is provided with a plurality of wave-like structures to form a handle.

3. The clipping device as set forth in claim 1, wherein said pushing block includes an upper section and a lower section, said upper section being a block body and said lower section being a flat rectangular plate, said clipping section being provided at an end of said lower section.

4. The clipping device as set forth in claim 3, wherein said upper section of said pushing block is a step-like structure.

5. The clipping device as set forth in claim 3, wherein a plurality of engraved elements are formed on said upper section of said pushing block.

6. The clipping device as set forth in claim 1, wherein said guiding mechanism are protruded edges respectively provided at both longitudinal edges of said slot.

7. The clipping device as set forth in claim 1, wherein said clipping section is a saw-like structure.

\* \* \* \* \*